United States Patent [19]
Dodson

[11] Patent Number: 4,795,447
[45] Date of Patent: Jan. 3, 1989

[54] ENDOTRACHEAL SUCTION CATHETER

[76] Inventor: Marian L. Dodson, 4500 15th St., Gulfport, Miss. 39501

[21] Appl. No.: 70,079

[22] Filed: Jul. 6, 1987

[51] Int. Cl.$^4$ ............................................. A61M 25/00
[52] U.S. Cl. .................................................. 604/268
[58] Field of Search ............... 604/104, 102, 266, 268; 128/207.15, 207.14

[56] References Cited

U.S. PATENT DOCUMENTS

| | | | |
|---|---|---|---|
| 1,611,385 | 12/1926 | Speer | 604/104 |
| 3,136,316 | 6/1964 | Beall | 604/268 X |
| 3,516,410 | 6/1970 | Hakim | 604/268 |
| 4,391,276 | 7/1983 | Lazarus et al. | 604/266 |
| 4,634,435 | 1/1987 | Ingraham | 604/268 |

*Primary Examiner*—Stephen C. Pellegrino
*Attorney, Agent, or Firm*—Alexander F. Norcross

[57] ABSTRACT

An improved endotracheal suction catheter significantly reduces the probability of segmental atelectasis or mucosal ingestion, by providing a number of spacing blades proximal the inserted tip of the catheter, of a size sufficient to prevent the tubular surface of the catheter from mucosal contact and to prevent bronchial collapse under suction. The tip of the catheter is closed and suction is applied through a plurality of openings located between and distal of the spacing blades. The blades insure continued suction flow throughout the bronchial structure, while preventing mechanical collapse of the bronchial structure or mucosal ingestion into the suction opening. The blades further serve to prevent excessive insertion of the catheter into the bronchial tree during intubation.

2 Claims, 2 Drawing Sheets

ENDOTRACHEAL SUCTION CATHETER

BACKGROUND OF THE INVENTION

This invention relates generally to catheters, specifically to endotracheal suction catheters, particularly of that class that are sterile, self-contained, and lubricated. The specific invention is of a form of such a catheter that, in use, significantly reduces the risk of segmental atelectasis distal to the catheter, and thus, significantly reduces the risk of trauma induced pneumonia in a patient.

In general, such a catheter is used on a postoperative, respiratory compromised, comatose, or anesthetized patient for suctioning liquid secretions which may occur within the bronchial system of the lungs. Such an application is usually a procedure performed in conjunction with other actions to maintain and restore proper breathing and oxygenation within this type patient.

The application of suction through a catheter within the bronchial system poses a constant risk of suction clamping of the catheter to the mucosa, with resulting trauma to the bronchial mucosal structure and the probability of swelling and/or bleeding occurring, increasing the risk of pneumonia. A more serious danger occurs because of the swelling of the mucosa and consequent restriction in the bronchial passageways incident to those medical conditions requiring the use of catheter suction to clear liquid from the lungs. The restricted bronchial passages raise a constant risk that an excessive insertion of the catheter will block the bronchia; and the suction will then collapse entirely that portion of the bronchial tree sealed off by the over-insertion of the catheter. Such a collapse is generally irreversible; the resulting segmental atelectasis results in reduction of the breathing capacity of the lung, subsequent pneumonia, and creates a high risk of mortality in the compromised patient.

The prevention of such segmental atelectasis during catheter use has been based on the skill of the treating medical personnel who, by estimate and experience, judge distance of insertion of the catheter. This cannot positively prevent the possibility of contact of the catheter with a mucosa and lining of the bronchial tubes.

The possibility of mucosal ingestion, with resulting trauma, by the suction apertures of the catheter has been recognized, and various forms of shielded drainage orifices have been developed to prevent or ameliorate this particular effect. Such prior developments include Lomholt, U.S. Pat. No. 4,227,529, which discloses a structure to reduce clamping of the catheter to the mucosa by suction and reduces the effect of mucosal damage. Earlier structures for shielded drainage orifices include Ericson, U.S. Pat. No. 3,435,827, and Beall, U.S. Pat. No. 3,136,316.

An inflatable cuff may be installed upon an endotracheal catheter to provide a tight seal at the entrance to the bronchial tree; the use of such an inflatable cuff is well known to prevent ingestion or passage of vomitus or fluid contaminate into the lungs of an anesthetized patient. A similar structure shown in Wallace, U.S. Pat. No. 2,749,913.

SUMMARY OF THE INVENTION

The current invention discloses a non-inflatable, rigid expansion member distal of the suction drain of an endotracheal suction catheter, but not forming the far tip thereof. The preferred form of the rigid extension, as shown, is an interdigitated extension having passages for the passage of a fluid.

The rigid expansion serves two purposes. The first is to provide for a physical offset or shielding of the suction drain of the catheter from the bronchial wall so as to prevent occlusion and suction of the mucosa and the resulting damage and deterioration to the bronchial tube surfaces. The second, and equally important effect, is to inhibit atelectasis distal to the catheter. The latter effect is known to occur if a suction catheter of a given size is so far inserted within the bronchial tree as to make sealing contact with the mucosa of a bronchial branch; the resulting trapped suction from the distal tip of the catheter causes a rapid and serious collapse of that portion of the bronchial tree distal of the catheter. Since a patient being suctioned has, by definition, inflammation of the mucosa or other deleterious, fluid producing conditions within the bronchial tree and the lungs, this collapse is in general significant and results in loss of function of the associated portion of the lung, and subsequent pneumonia.

The interdigitated expansion section distal of the suction drain on the inventive catheter prevents the creation of a closed, sealed area which can be collapsed. The interdigitated form of the expansion permits continued fluid flow into the catheter and preserves suctioning while preventing total mucosal closing about the catheter.

It is, therefore, an object of this invention to provide a means for positive prevention of segmental atelectasis distal to an endotracheal catheter and to inhibit catheter suction hole attachment to the mucosal surface of the bronchial tree.

DETAILED DESCRIPTION OF THE PREFERRED EMBODIMENT

Figure 1:
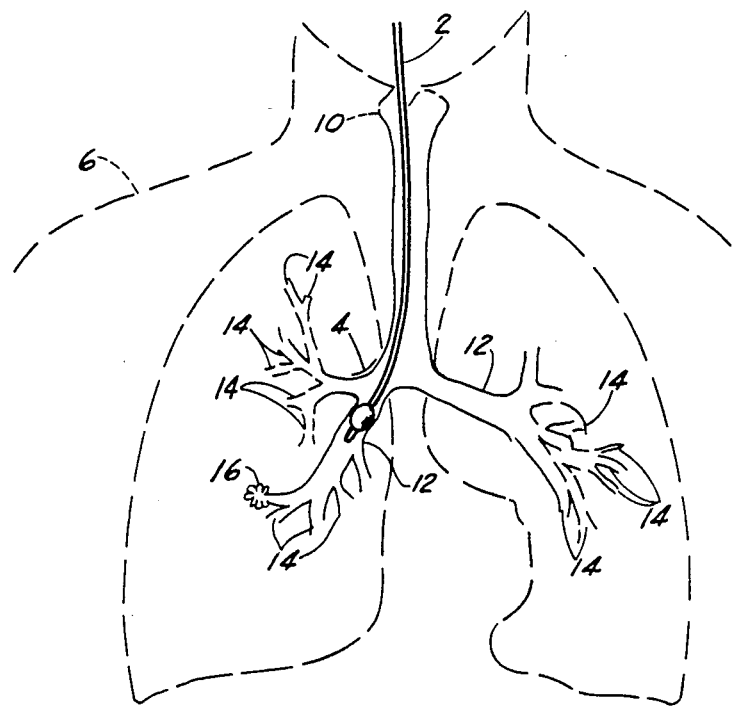
FIG. 1 depicts an outline of a bronchial tree being suctioned by an endotracheal catheter of the current invention, the collar of the invention being exaggerated in size for illustrative purposes.
Figure 3:
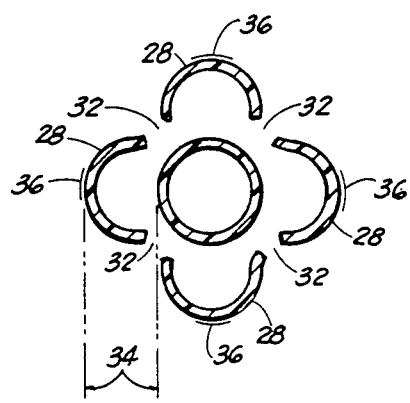
FIG. 3 shows a dual section through the outer perimeter of the expanded collar of the invention and through the distal tip of the inventive catheter.
Figure 2:
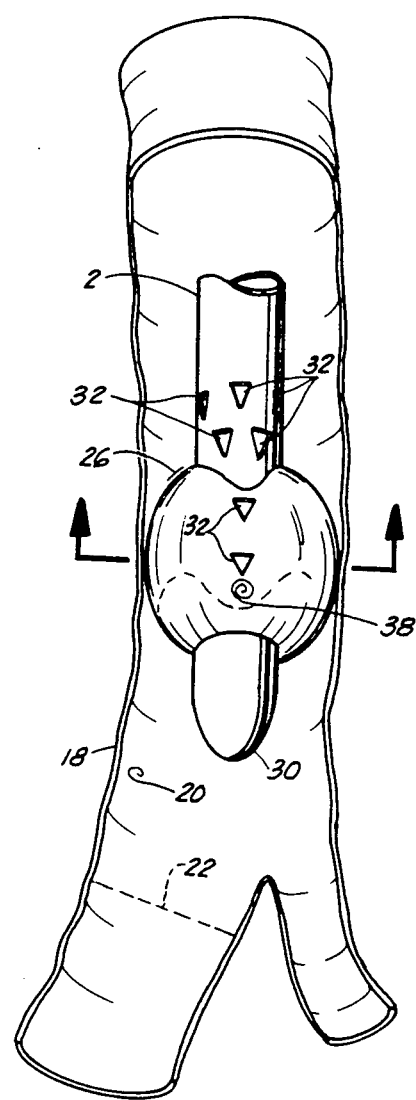
FIG. 2 shows the distal tip of an endotracheal suction catheter of the invention in the preferred form inserted within a branch of the bronchial tree.

Referring to the figures, which are illustrative, and as such omit depiction of other medical apparatus which those skilled in the art would normally expect to be employed either as part of the process of intubation of a respiratorally compromised patient, and the use of which is well known in the art, but which are omitted here in order to provide a clearer set of drawings, it is seen that the endotracheal catheter 2 is, in the process of intubation, inserted into the bronchial tree 4 of a respiratorally compromised patient 6 for the purpose of suctioning fluids and secretions (not shown).

The use of an endotracheal catheter of the type consisting of a long, flexible, hollow tube of constant diameter is well known in the art for this purpose; the diameter of the tube is referred to as a series of standardized numeric sizes denoted by the appellation French followed by a number, for example, French 6, French 8, etc. The designation refers to increasing diametric sizes in the catheter.

As is well known, the bronchial tree 4 of the patient is so named because of its resemblance in construction to a standard tree, that is, the trachea 10 branches into two major bronchial segments 12 which in turn through a process of repeated branching become larger numbers of smaller bronchi which ultimately connect to the alluvial sacs of the lung 16 in which the basic oxygen/carbon dioxide osmotic interchange occurs. The bronchi 14 provide the flow path for air into the lungs and thus must be kept clear and unblocked to provide full respiratory capacity to an individual.

It is known that the bronchi internal surface is a relatively stiff outer supporting tubular structure 18 whose inner surface is coated by a mucosal surface 20, which in the healthy lung maintains a moist coating protecting the cellular structure of the bronchi from exposure to air.

In the respiratorally compromised or diseased patient, the mucosal surface 20 swells, emitting greater mucosal secretions, thus reducing the internal diameter 22 of the bronchi 14, ultimately contributing to the filling of the bronchi with the liquid fluids and secretions which significantly reduce the respiratory capability of the lung. The mucosal surface 20 and associated mucosa are moist, have a relatively high viscosity and are fairly adhesive; the combination therefore readily permits the creation of air tight seals between the tubes of an endotracheal catheter and the bronchial wall, creating a closed section of the bronchial tree which is then exposed to full suction from the catheter. While such a sealing capability can be advantageous, and is utilized by the prior art inflatable cuffs to isolate the bronchial tree from the esophagal structure so as to prevent the ingestion and re-breathing of vomitus in the comatose patient, if such a closed section is formed during the course of catheterization and suctioning of the patient, it promotes an immediate segmental collapse of the sealed portion of the bronchial tree.

Once such a collapse has occurred, the joining of the mucosal surfaces 20 is in general irreversible, resulting in segmental atelectasis, pneumonia, and other more serious complications in the patient.

The inventive form of the endotracheal catheter 2 is provided with a separator blade structure 26. This blade structure 26 comprises in turn at least two individual stabilizing blade members 28 which are rigid in the sense that they are at least as resistent to bending as is the basic endotracheal suction catheter tube 2, although they need not be so rigid as to be brittle or as to inhibit the positioning of the endotracheal catheter 2. The blade structure 26 is located proximate the tip 30 of the endotracheal catheter 2, which tip is closed against suction. The tip 30 provides rather a guiding capability to permit the ready guiding of an endotracheal catheter 2 through an ever decreasing network of bronchi 12, 14 in the bronchial tree for ready insertion.

Within the endotracheal catheter 2 are provided suction vents 32 or openings through the wall of the endotracheal catheter 2 for the transmission of suction from within the endotracheal catheter to the bronchial structure. It is well understood that the endotracheal catheter 2 is itself a hollow tube at the non-inserted end connected to a source of suction.

The suction openings 32 in the inventive endotracheal catheter are not located at the tip but rather are located so that they are between the individual stabilizing blade members 28 or distal of the blade members 28, but none of them are located more closely to the tip than are located the blade members 28.

Each of the blade members 28, are of a height 34 as to maintain a positive separation between the mucosal surface 20 and the suction openings 32. This height which may typically be equivalent to the radius of the basic tube 2 must be sufficient to permit continued suction and airflow into the suction openings 32 while the blade contact edge 36 is in contact with the mucosal surface 20. In distinction to the prior art which provides various forms of collapsible or resilient screens for closing off the suction opening, the separator blade structure 26 of the current invention must be rigid and must maintain, without collapsing, this open airflow.

In use, the endotracheal catheter 2 of the current invention is utilized in a manner well understood in the art, being connected at a distal end to a source of suction and then being manually inserted through the trachea into the bronchial tree for suctioning of secretions within the lung.

In the prior art, the distance the catheter was inserted was a matter of the individual skill of the medical personnel performing the procedure. In the current case the catheter may be inserted in the bronchial tree to a point where the stabilizer blade outer contacting edges 36 uniformly contact the mucosal surface 20 of a particular bronchi 14. This physical contact, being felt by the practitioner, indicates a positive limit to further insertion of the catheter. The height 34 of the blades maintains a positive airflow space 38 within the bronchi 14 both above the catheter tip as well as within the bronchi below the insertion of the catheter. This positive airflow permits continued suctioning through the suction opening 32 while the blade height 34 prevents ingestion of the mucosal structure into the suction openings and thus prevents damage to the mucosa. More importantly, the airflow space 38, being open both above as well as below the catheter, prevents the formation of a flow closed section 24 of the bronchial tree and thus prevents the formation of a negative pressure within the bronchi such as would create segmental atelectasis.

Because of the positive tactile feedback upon contact provided by the separator blade structure 26, the use of the catheter and the prevention of excessive insertion is considerably easier. More importantly, however, the rigid blade structure 26 in combination with the placement of the suction openings 32 positively prevents the formation of closed, sealed sections of the bronchial tree and thus prevents suction induced collapse of the bronchi and the resulting deterioration of the patient's condition.

While the preferred embodiment of the invention described shows in the figure four relatively thick blades, it should be apparent that the thickness of a blade is relatively immaterial so long as they are not so thin as to create a cutting effect; it should further be obvious that so long as the blades are substantially symmetrically and radially disposed about the axis of the endotracheal catheter, that any number of blades, so long as there are at least two, is suitable. Thus the exact form of the invention is not the preferred embodiment here disclosed but that wider range of equivalents encompassed by the claims below.

I claim:

1. An endotracheal suction catheter comprising:
   a. an elongate, hollow, flexible tube having a substantially uniform cross-section, having a first closed and second open end connected to a suction source;
b. at least two substantially rigid non-cutting blade means, (proximate said first closed end), radially extending an outer distance from said tube extending lengthwise along said tube from a point proximate said closed end;
c. said blade means being symmetrically, radially disposed about said tube maintaining said tube in a spaced distance relationship to tracheal mucosal structure;
d. (a plurality of) at least one suction openings through the wall of said tube, (proximate) between said blade means, distal said closed end;
e. said tube, said blade means and said suction openings thereby forming an open non-sealing passage along said tracheal structure for continued flow of air.

2. The apparatus as described in claim 1 above wherein said blade means further comprise:
a. a first, substantially rigid, smoothly rounded linear member, radially extending in a direction outward from the axis of the tube for a distance substantially equivalent to or greater than the radius of the tube;
b. at least one second extension means, diametrically opposed to said first extension means;
c. said suction openings being intermediate said extension means(.);
d. said extension means being of a width such that all suction openings are maintained in a spaced apart relation to the tracheal mucosal structure.

* * * * *